United States Patent
Balzano

(10) Patent No.: US 8,353,085 B2
(45) Date of Patent: Jan. 15, 2013

(54) SANITARY HANDLE COVER

(75) Inventor: Alfiero Balzano, Garden Grove, CA (US)

(73) Assignee: Basic Electronics, Inc., Garden Grove, CA (US)

(*) Notice: Subject to any disclaimer, the term of this patent is extended or adjusted under 35 U.S.C. 154(b) by 83 days.

(21) Appl. No.: 12/964,661

(22) Filed: Dec. 9, 2010

(65) Prior Publication Data

US 2012/0144610 A1  Jun. 14, 2012

(51) Int. Cl.
*E05B 1/00* (2006.01)
*A45C 13/26* (2006.01)

(52) U.S. Cl. .............. 16/441; 16/422; 16/904; 16/110.1

(58) Field of Classification Search ................ 16/110.1, 16/111.1, 905, 903, 904, 422, 425, 435; 4/246.1; 15/244.3, 244.4, 104.92, 104.93; 292/1, 292/347; 250/454.11; 150/154, 155; 221/45, 221/46; 206/233; 280/33.991, 33.992, 33.993
See application file for complete search history.

(56) References Cited

U.S. PATENT DOCUMENTS

| | | | | |
|---|---|---|---|---|
| 4,832,942 A | * | 5/1989 | Crace | 428/41.1 |
| 4,856,140 A | | 8/1989 | Visco et al. | |
| 4,869,305 A | * | 9/1989 | Jones | 150/155 |
| 4,975,826 A | * | 12/1990 | Bell | 362/376 |
| 5,701,635 A | * | 12/1997 | Hawkes | 16/421 |
| 5,713,615 A | * | 2/1998 | Tsai | 292/347 |
| 6,546,594 B1 | * | 4/2003 | Wills | 16/412 |
| 6,796,002 B2 | * | 9/2004 | Beckwith | 16/422 |
| 2004/0266546 A1 | * | 12/2004 | Huang | 473/300 |
| 2006/0006678 A1 | * | 1/2006 | Herron | 292/336.3 |
| 2006/0010652 A1 | * | 1/2006 | Kellaher et al. | 16/413 |
| 2006/0230576 A1 | * | 10/2006 | Meine | 16/110.1 |

FOREIGN PATENT DOCUMENTS

| | | | | |
|---|---|---|---|---|
| EP | 2098664 A1 | * | 9/2009 | |
| FR | 2590797 A3 | * | 6/1987 | |
| JP | 09137644 A | * | 5/1997 | |
| JP | 09324366 A | * | 12/1997 | |

\* cited by examiner

*Primary Examiner* — Chuck Y. Mah
(74) *Attorney, Agent, or Firm* — Stetina Brunda Garred & Brucker

(57) ABSTRACT

Provided is a sanitary handle cover configured to store and dispense sanitary fluid in response to pressure being applied to the handle cover, such as when an individual grabs the handle cover to open the door. The handle cover may additionally be adapted to be quickly and easily placed over the handle and substantially conform to the shape of the handle to remain on the handle during use.

11 Claims, 3 Drawing Sheets

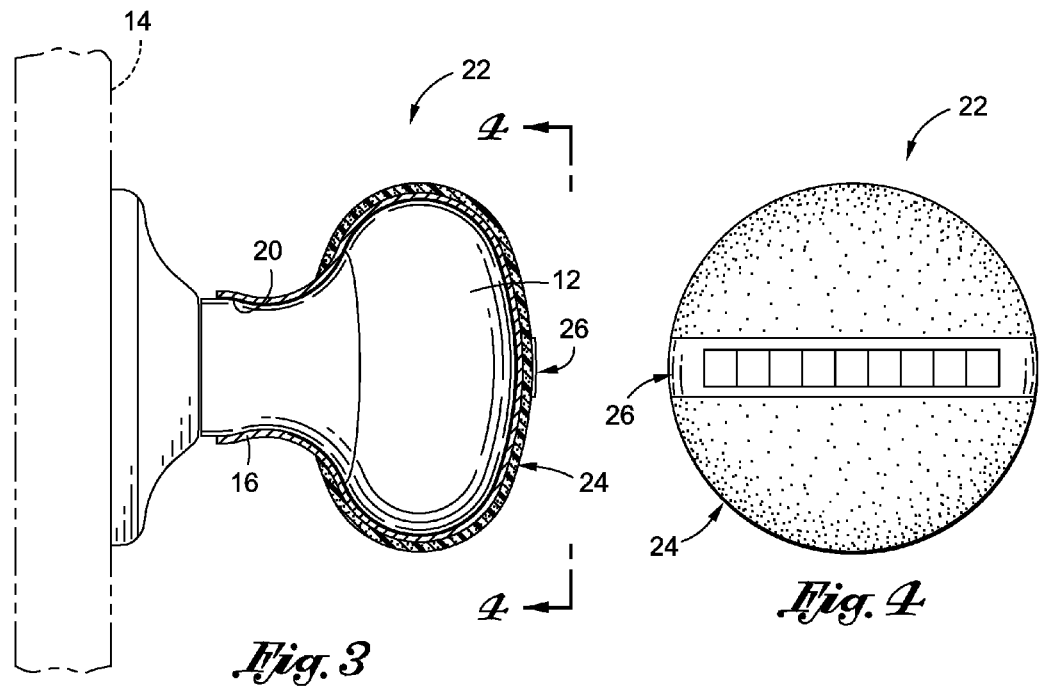
Fig. 3
Fig. 4
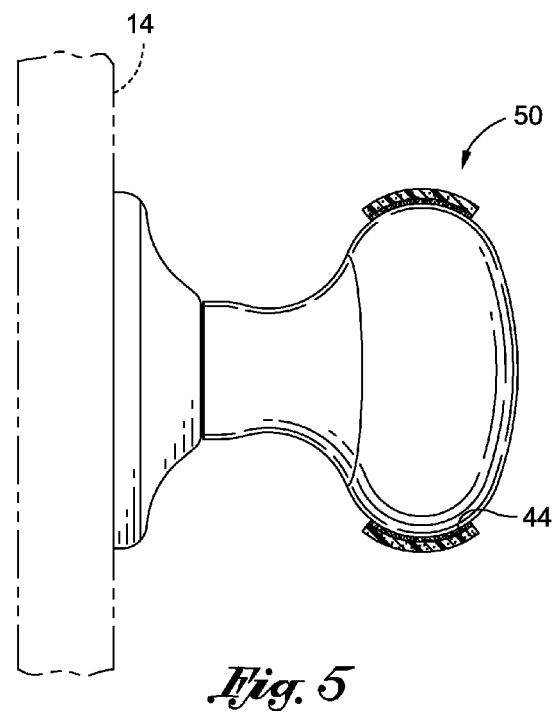
Fig. 5

SANITARY HANDLE COVER

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention relates generally to hygienic devices, and more particularly, to a novel cover for mounting on or over handles, wherein the cover dispenses a quantity of sanitizer on the user's hand in response to pressure being applied to the cover (i.e., the user grabbing the handle).

It is the normal practice to open doorknobs or depress toilet flushing handles by grasping the knob or handle with the fingers and grabbing tightly to complete a turning or depressing procedure. As multiple users grab the knob or handle, the knob or handle may become contaminated with germs, bacteria, etc., which may facilitate the transfer of disease. As such, it is well known that the spread of disease may be mitigated by reducing such contamination.

One possible method of reducing contamination is to provide sanitizing fluids near the doorknobs or handles to substantially cleanse the user's hand before the user grabs the doorknob or handle. A sanitizing dispenser may be placed near the handle to allow the user to sanitize his hands before engaging with the doorknob or handle. One drawback associated with this method is that it relies upon each individual to sanitize his/her hands before engaging with the doorknob or handle. Oftentimes individuals are in a hurry and forget the sanitization step, or are unaware of the location of the dispensing unit. In each case, one or more individuals may grab onto the handle or knob without sanitizing his or her hands.

Another contamination reducing method may include routinely sanitizing the handles or doorknobs to clean the surface of the handles or doorknobs from the germs, bacteria, etc. Sprays or disinfectant substances may be employed by maintenance personnel by rubbing or otherwise attempting to cleanse the external surface of the knob or handle. This procedure tends to be unsuccessful since it is generally cumbersome and requires routine upkeep. Furthermore, maintenance personnel typically only visit the knob or handle location periodically throughout a time period, and therefore, no assurance may be given to the user than the knob is in a sanitary condition at all times.

Another technique which may be employed to reduce contamination is to form a temporary barrier around the doorknob or handle. In this regard, a rubber, plastic, or paper cover may be disposed over the handle for a short period of time to protect the handle from users which grab the handle. The cover may be pre-shaped to fit over a handle or knob having a specific size and shape. After a period of time, the cover/barrier may become soiled as several users grab the handle or knob. Accordingly, the cover may be removed and replaced with a new cover. A common drawback with such a technique is that barrier-type covers do not sanitize the handle or hand of the user. Therefore, germs or bacteria may linger on the cover and be passed on to subsequent users. In addition, uniquely shaped handles or knobs may present a problem for this technique because the covers may not be specifically sized to accommodate the unique shape defined by such handles.

Therefore, a long standing need has existed to provide a novel means for maintaining a sanitary external surface of a doorknob or flushing handle to protect the fingers of the user from coming into substantial contact with contaminated surfaces of the knob or handle. Furthermore, there exists a need for providing a more readily accessible and easy to use sanitizing dispenser which may sanitize a user's hands and/or a handle or knob to mitigate the transfer disease. The present invention addresses this particular need, as will be described in more detail below.

BRIEF SUMMARY

There is provided a sanitary handle cover configured to store and dispense sanitary fluid in response to pressure being applied to the handle cover, such as when an individual grabs the handle cover to open the door. The handle cover may additionally be adapted to be quickly and easily disposed over the handle to insertably receive the handle and to substantially conform to the shape of the handle to remain on the handle during use.

According to one implementation, the handle cover includes a base layer defining a pocket configured to receive the handle. The pocket may be conformable to the size and shape of the handle upon receipt of the handle within the pocket. An absorbent layer is connected to the base layer and is configured to store sanitizer and to dispense the sanitizer in response to pressure applied to the absorbent layer.

The handle cover may include an indicator in operative communication with the absorbent layer. The indicator is configured to emit a visual signal corresponding to the amount of sanitizing fluid in the absorbent layer (i.e., the indicator signal changes as the sanitizer levels drop).

According to another embodiment, it is contemplated that the sanitizing handle cover includes an internal bladder configured to store and dispense the sanitizer. More specifically, the handle cover includes an inner layer configured to receive the handle and to be conformable to the size and shape of the handle. A perforated outer layer is disposed over the inner layer such that the inner and outer layers collectively define the bladder. The outer layer includes a plurality of perforations and defines a resiliency which biases the perforations toward a closed position. The outer layer is moveable in response to pressure being applied thereto to open at least one perforation for dispensing a quantity of the sanitizing fluid.

It is additionally contemplated that the sanitizing handle strips may be provided for placement on handles having unique shapes which may not accommodate standard handle covers. The sanitizing strips may include an absorbent layer or an internal bladder for storing and dispensing the sanitizer. The strips may also be flexible to allow the strips to conform to the unique contours of the handles upon which the strips may be placed.

The present invention is best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 3 is a cross sectional view of another embodiment of a sanitary handle cover having an indicator for displaying the amount of sanitizer contained within the handle cover;

FIG. 4 is a front view of the sanitary handle cover depicted in FIG. 3;

FIG. 5 is a cross sectional view of a sanitary handle cover strip similar to the sanitary handle cover depicted in FIG. 3;

DETAILED DESCRIPTION

Figure 1:
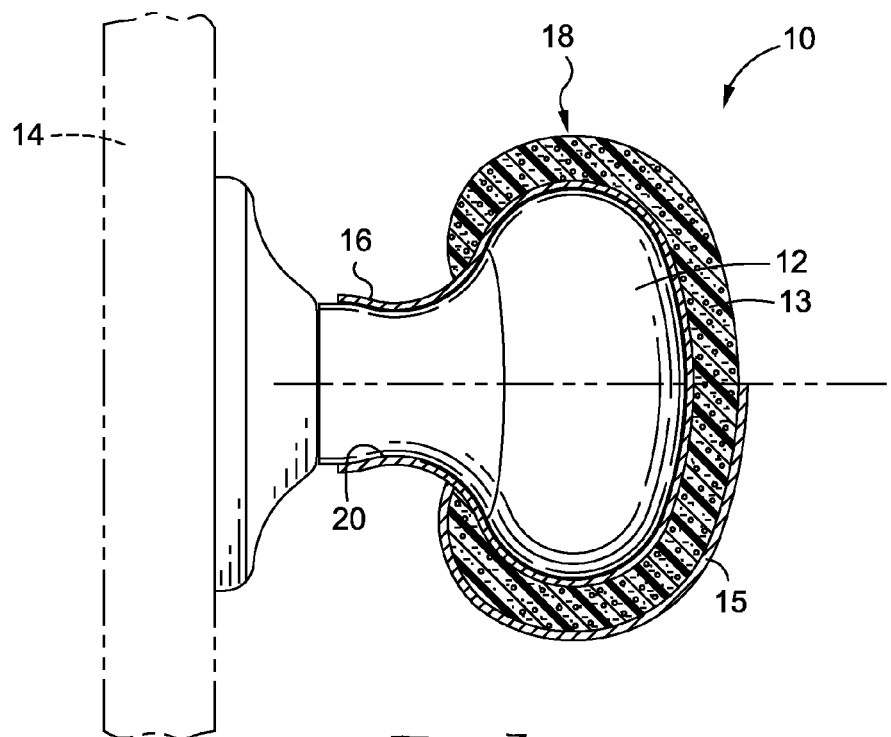
FIG. 1 is a cross sectional view of a sanitary handle cover having a sponge-like layer configured to store and dispense sanitizer.

Referring now to the drawings, wherein the showings are for purposes of illustrating a preferred embodiment of the present invention only, and not for purposes for limiting the same, there is shown a sanitary handle cover 10 disposed on a handle 12. The handle cover 10 is configured to dispense a sanitizer 13 in response to a user grabbing the handle cover 10 during the normal procedure of opening the door 14. In this regard, the handle cover 10 acts as a storage device for the sanitizer 13 and is conveniently to provide a sanitary surface upon which users may engage with when opening/closing the door 14 to mitigate the transfer of disease. The sanitizing handle cover 10 is an improvement over many existing handle covers and sanitizing techniques, which generally include handle covers which merely serve as a barrier between the handle 12 and the user's hand, or sanitizing dispensers, which may be located remote from the handle 12 and thus may be difficult to see before a user grabs for the handle 12. In most cases, the improved handle cover 10 is positioned directly on the handle 12 such that the handle cover 10 must be grabbed by user to actuate the handle 12 to open the door 14. In the process, the user's hand will be sanitized, and the handle 12 will be protected from any contaminants or germs which may be present on the user's hand.

Referring now specifically to the embodiment depicted in FIG. 1, the handle cover 10 is disposed over a handle 14 to insertably receive the handle 14 within the cover 10. As used herein, the word "handle" may refer to a door knob, handle on a toilet, or other structural members which may be grasped by a user's hand to open, close, or actuate a related article (such as a door 14).

The handle cover 10 includes a base layer 16 and an absorbent layer 18 connected to an outer surface of the base layer 16. The base layer 16 defines a pocket 20 configured to receive the handle 12. The base layer 16 may be conformable to the size and shape of the handle 12. In this regard, the pocket 20 may define a size which is larger than the handle 12 prior to the cover 10 being disposed over the handle 12 to allow the handle 12 to be insertably received within the pocket 20. Once the handle 12 is received within the pocket 20, the base layer 16 may collapse upon the handle 12 to conform to the shape thereof. In this regard, the base layer 16 may be formed from a material which is easily formable to compliment the shape of the handle 12.

The base layer 16 may have inherent properties which cause the base layer 16 to collapse upon the handle 12 when the handle 12 is received within the pocket 20. For instance, the base layer 16 may define an elasticity or resiliency which allows the base layer 16 to conform to the shape of the handle 12. Latex, rubber or other elastic materials may be used to form such a base layer 16. Alternatively, the base layer 16 may be configured to allow a user to form the base layer 16 around the handle 12 when the handle 12 is received within the pocket 20. For example, the base layer 16 may be formed from paper, wherein the paper is folded around the handle 12 to conform to the shape of the handle 12.

The base layer 16 may be configured to mitigate removal of the handle cover 10 from the handle 12 once the handle cover 10 is disposed on the handle 12. Along these lines, the base layer 16 may be formed from a rubber material which may create a frictional engagement with the handle 12 once placed on the handle 12. However, adhesives may also be applied to the base layer 16 to secure the handle cover 10 to the handle 12. This may be particularly advantages for base layers 16 which do not inherently secure the handle cover 10 to the handle 12. For instance, a base layer 16 formed of a paper material may have a low-shear adhesive disposed thereon to mitigate movement of the handle cover 10 relative to the handle 12. Other fastening elements known in the art, such as rubber bands, tape, etc. may also be used to secure the handle cover 10 to the handle 12.

The absorbent layer 18 is connected to the base layer 16 such that when the cover 10 is disposed on the handle 12, the absorbent layer 18 is positioned over the primary gripping areas of the handle 12 (i.e., the areas of the handle 12 which are most commonly gripped). For instance, as depicted in FIG. 1, the handle 12 includes a bulbous portion which a user grabs to open the door 14. Therefore, the absorbent layer 18 is disposed over the bulbous portion so that when a user grabs the handle 12, the user's hand engages with the absorbent layer 18.

A sanitizer 13 (depicted in FIGS. 1-2 as small circles) is stored within the absorbent layer 18. The sanitizer 13 may be a liquid, powder, or other known sanitary product. The sanitizer 13 may be impregnated, absorbed, or otherwise disposed and stored within the absorbent layer 18. According to one embodiment, the absorbent layer 18 is a porous, sponge-like layer to facilitate such storage and dispensing of the sanitizer 13. In particular, the pressure responsive, absorbent layer 18 is configured to dispense the sanitizer 13 in response to pressure applied to the absorbent layer 18, such as when a user grabs onto the handle 12.

The base layer 16 may be formed from a fluid impermeable material, such as rubber, or include a fluid resistant coating to the keep the sanitizing fluid within the absorbent layer 18 and to protect the handle 12 from the sanitizing fluid. For instance, the sanitizing fluid may cause corrosion, warping, or other structural damage to the handle 12.

It is contemplated that users may have dirt or debris present on their hands when they reach for the handle cover 10. Furthermore, given the absorbent qualities of the absorbent layer 18, the dirt or debris may be easily transferred to the absorbent layer 18. Accordingly, one embodiment of the handle cover 10 includes an external layer 15 (See FIG. 1) disposed over the absorbent layer 18 to mitigate dirt/debris transfer from the user's hands to the absorbent layer 18. The external layer 15 may not absorb the dirt/debris as readily as the absorbent layer 18 would, yet at the same time, may be configured to allow the sanitizer 13 to pass therethrough when the user grabs onto the handle 12. In this regard, the external layer 15 may be configured to fluidly communicate the sanitizer 13 from the absorbent layer 18 to the user's hand. For instance, the external layer 15 may be configured to allow the sanitizer 13 to seep therethrough or the external layer 15 may include openings which the sanitizer 13 may pass through. Exemplary external layers 15 may be formed from cotton fabric or rubber with perforations; however, other materials known by those skilled in the art may be used without departing from the spirit and scope of the present invention.

The handle covers 10 may be pre-shaped to fit over handles 12 defining a particular size or shape. The pre-shaped covers 10 may also be stacked for packaging within a bottle or tube. In this regard, several handle cover 10 may be sold within a single package. The package may be fluidly sealed to mitigate evaporation of the sanitizing fluid stored within the absorbent layer 18.

Referring now specifically to FIGS. 3-4, there is shown another embodiment of a handle cover 22 having an thinner profile than the handle cover 10 depicted in FIG. 1. In particular, the absorbent layer 24 is formed from an absorbent fabric, rather than a sponge-like material. The absorbent fabric may mitigate some of the dirt/debris transfer concerns noted above, but may not have the absorbent capacity of the sponge-like material shown in FIG. 1. The thin profile of the absorbent fabric may allow the handle cover 10 to be more adaptable to the size and shape of the handle 12 (i.e., it may have more flexibility to conform to the unique contours of the handle 12).

After the handle cover 22 has been disposed on the handle 12 for a period of time, the sanitizer 13 contained within the absorbent layer 24 may dry up, either from evaporation or extensive use. Therefore, various embodiments of the cover 10 may include an indicator 26 which emits a visual signal corresponding to the amount of sanitizer 13 contained within the absorbent layer 24. The indictor 26 is in fluid communication with the absorbent layer 24 to detect the amount of sanitizer 13 present within the absorbent layer 18. The indicator 26 may be configured to emit various signals as the amount of sanitizer decreases. For instance, the indicator 26 may be invisible or transparent when there are high levels of sanitizer 13 within the absorbent layer 24. As the sanitizer 13 decreases, the indicator 26 may define a bold color to alert maintenance personnel that the sanitizer level is low. Those skilled in the art will appreciate that other indicator signals may be emitted without departing from the spirit and scope of the present invention.

When the sanitizing levels are low, the cover 22 may be removed from the handle 12 and replaced with a new cover 22 having high sanitizer levels. Alternatively, the absorbent layer 24 may be refilled with sanitizer 13 to bring the sanitizer levels up to an operative amount. For instance, sanitizing fluid may be sprayed or coated on the absorbent layer 24 to refill the cover 22. When the absorbent layer 24 is refilled, the signal emitted by the indicator 26 may change to reflect the increased level of sanitizer 13. Those skilled in the art will appreciate that use of the indicator 26 is not limited to cover 22, and that the indicator 26 may be used with other covers, especially cover 10 discussed above, and cover 30 discussed below.

Figure 6:
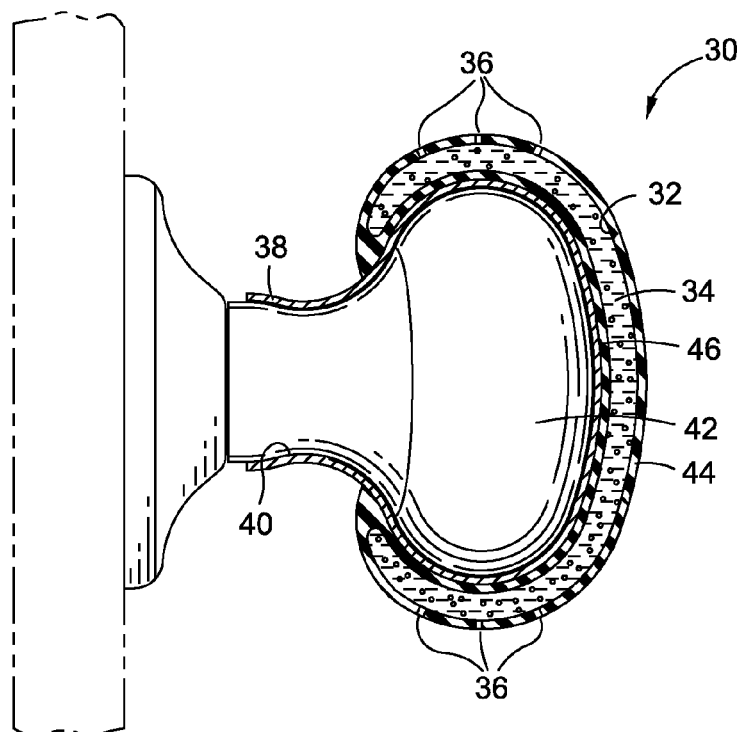
FIG. 6 is a cross sectional view of a sanitary handle cover having an internal bladder configured to store and dispense sanitary fluid.

Referring now to FIG. 6, there is shown another embodiment of a handle cover 30 which includes an inner bladder 32 for storing sanitizer 34. The inner bladder 32 is configured to dispense the sanitizer 34 in response to pressure applied to the cover 30 when the user grabs onto the cover 30. More specifically, the pressure causes the sanitizer 34 to seep through perforations 36 formed within the cover 30.

The cover 30 may provide a desirable alternative to the cover 10 discussed above because the cover 30 may include an outer surface which is not absorbent thereby allowing the cover 30 to be cleaned or wiped off should it become dirty. In this regard, the cover 30 may be suitable in environments where debris or moisture is present and can be wiped off the surface of the cover 30. For instance, the cover 30 may be suitable for handles in a machine shop, handles located outside, or handles located near a pool.

The cover 30 includes an inner layer 38 defining a pocket 40, similar to the base layer 16 and pocket 20 discussed above in relation to the cover 10. The inner layer 38 is configured to be conformable to the size and shape of the handle 42 upon receipt of the handle 42 within the pocket 40.

The cover 30 additionally includes a perforated outer layer 44 having a plurality of perforations 36 formed therein. The outer layer 44 and the inner layer 38 collectively define the bladder 32. The outer layer 44 is preferably formed from a fluid impermeable material, such as rubber, to mitigate unwanted loss of the sanitizer 34 therethrough. In the embodiment depicted in FIG. 6, the inner layer 38 includes a coating 46 coupled to the outer layer 44 to provide a fluid impermeable boundary to the inner layer 38.

The outer layer 44 is preferably elastically deformable to facilitate opening and closing of the perforations 36. More specifically, it is desirable to keep the perforations 36 in a closed configuration when the cover 30 is not being grasped by a user to keep the sanitizer 34 within the bladder 32. However, it is also desirable to selectively open the perforations 36 to dispense the sanitizer 34 to the user's hand. Accordingly, the bladder 32 is configured such that when the user grasps the handle cover 30, and applies pressure to the handle cover 30 by squeezing the handle cover 30, the outer layer 44 will slightly deform and exert a pressure on the sanitizer 34. Accordingly, a quantity of the sanitizer 34 will be urged to flow through one or more of the perforations 36 and onto the user's hand.

The outer layer 44 of the bladder 32 may be clear or transparent to allow maintenance personnel to determine the sanitizer levels of the cover 30 upon visual inspection of the cover 30. When the bladder 32 is empty, the cover 30 may be replaced or the bladder 32 may be refilled with a refilling tool having a refilling straw which is inserted through one of the perforations 36 to access the bladder 32. Once the bladder 32 is refilled, it may continue storing and dispensing sanitizer 34.

In addition to the foregoing, it is understood that handles may define very unique shapes and contours which may be difficult to fit a sanitizing cover over. Therefore, referring now to FIGS. 2, 5, and 7, there is shown sanitizing strips which may be disposed on a uniquely shaped handle to store and dispense sanitizer in response to a user grabbing the sanitizing strip. The sanitizing strips are configured to have a degree of flexibility to allow the strips to conform to the unique contours of the handles. Furthermore, several strips may be packaged as a sheet of strips, which may be individually torn off for use.

Figure 2:
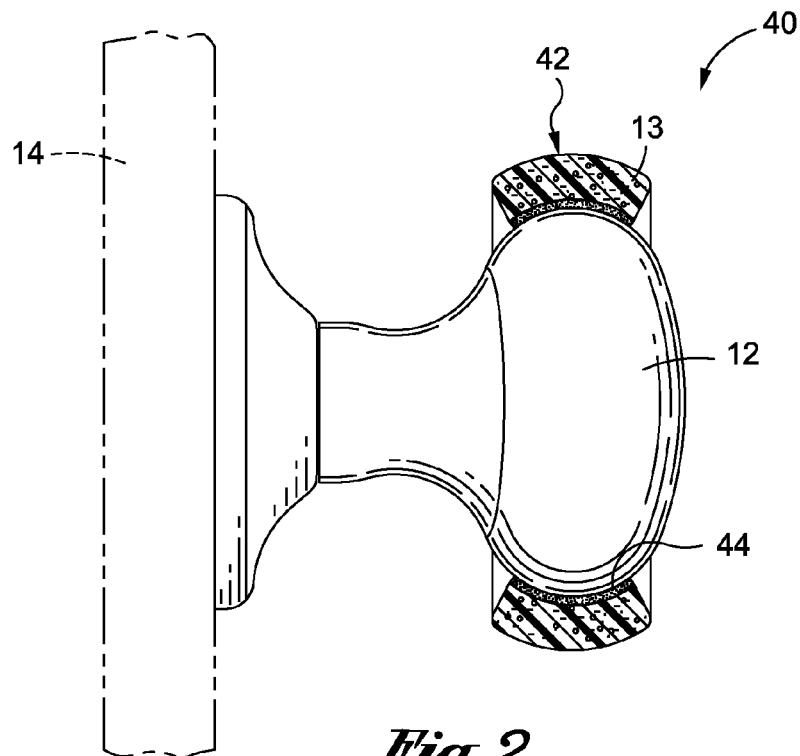
FIG. 2 is a cross sectional view of a sanitary handle cover strip having a sponge-like layer configured to store and dispense sanitizer.

Referring now specifically to FIG. 2, there is shown a sanitizing strip 40 having an absorbent layer 42 similar to the absorbent layer 18 shown in FIG. 1. In this regard, the pressure responsive, absorbent layer 42 is formed from a porous, sponge-like material configured to absorb sanitizer and dispense sanitizer in response to pressure being applied to the absorbent layer. An adhesive layer 44 is connected to the absorbent layer 42 and is configured to couple the sanitizing strip 40 to the handle. The adhesive layer 44 may include a low-shear adhesive, or other types of fasteners, such as hook and loop type fasteners to secure the strip 40 to the handle 12.

Figure 7:
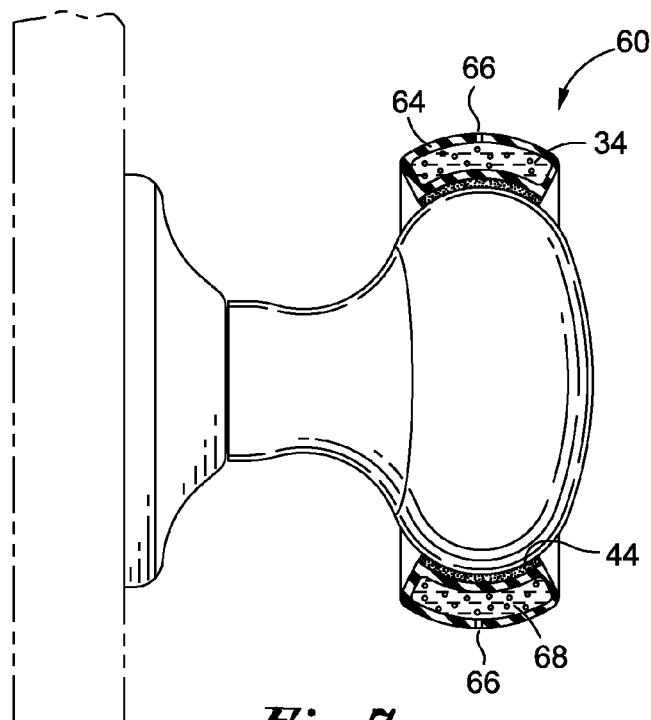
FIG. 7 is a cross sectional view of a sanitizing handle strip having an internal bladder configured to store and dispense sanitary fluid.

FIG. 5 depicts a sanitizing strip 50 having an absorbent layer 52 similar to the absorbent layer 18 shown in FIG. 3. An adhesive layer 44 is connected to the absorbent layer 52 to connect the sanitizing strip to the handle. Furthermore, FIG. 7 shows a sanitizing strip 60 having an inner bladder 62 similar to the inner bladder 62 similar to the inner bladder 32 shown in FIG. 6 for storing and dispensing sanitizing fluid. In this regard, the sanitizing strip 60 includes an outer layer 64 having perforations 66 formed therein through which the sanitizer 68 may be dispensed therefrom. Adhesive layer 44 connects the sanitizing strip 60 to the handle.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A sanitizing handle cover configured for use with a handle, the handle cover comprising:
   a base layer defining a pocket configured to receive the handle, the base layer being configured to be conformable to the size and shape of the handle upon receipt of the handle within the pocket;
   a sanitizer;
   a pressure responsive, absorbent layer connected to the base layer, the absorbent layer being configured to store the sanitizer and to dispense the sanitizer in response to pressure applied to the absorbent layer; and
   an indicator in operative communication with the absorbent layer, the indicator being configured to emit a visual signal corresponding to the amount of sanitizer in the absorbent layer.

2. The sanitizing handle cover as recited in claim 1, wherein the base layer is elastically deformable to facilitate receipt of the handle within the pocket.

3. The sanitizing handle cover as recited in claim 2, wherein the base layer conforms to the handle in response to the handle being received within the pocket.

4. The sanitizing handle cover as recited in claim 1, wherein the base layer is fluid impermeable.

5. The sanitizing handle cover as recited in claim 1, further comprising an adhesive disposed on the base layer to mitigate movement of the base layer relative to the handle upon receipt of the handle within the pocket.

6. The sanitizing handle cover as recited in claim 1, wherein the absorbent layer defines a moisture level correlated to the amount of sanitizer absorbed, the absorbent layer being in fluid communication with the indicator, the indicator being configured to emit the visual signal in response to the moisture level falling below an operative moisture level.

7. The sanitizing handle cover as recited in claim 1, wherein the handle cover is configured to be stackable to enable a plurality of handle covers to be disposed in a stacked configuration.

8. The sanitizing handle cover as recited in claim 1, wherein the absorbent layer is formed of a porous material.

9. The sanitizing handle cover as recited in claim 1, further comprising a fluid permeable cover layer disposed over the outer surface of the absorbent layer and in fluid communication with the absorbent layer.

10. The sanitizing handle cover as recited in claim 9, wherein the cover layer is formed from a cotton fabric material.

11. The sanitizing handle cover as recited in claim 9, wherein the cover layer is formed from a paper material.

* * * * *